(12) United States Patent
House

(10) Patent No.: US 7,266,209 B1
(45) Date of Patent: Sep. 4, 2007

(54) COCHLEAR IMPLANTS WITH A STIMULUS IN THE HUMAN ULTRASONIC RANGE AND METHOD FOR STIMULATING A COCHLEA

(76) Inventor: David William House, 23022 Yeary La. NE., Aurora, OR (US) 97002

( * ) Notice: Subject to any disclaimer, the term of this patent is extended or adjusted under 35 U.S.C. 154(b) by 0 days.

(21) Appl. No.: 09/478,136

(22) Filed: Jan. 5, 2000

(51) Int. Cl.
*H04R 25/00* (2006.01)
(52) U.S. Cl. .................. 381/331; 381/312; 381/326
(58) Field of Classification Search ............ 381/326, 381/331, 151, 316, 312, 315; 600/25, 559; 607/55–57, 137; 455/40, 41, 43
See application file for complete search history.

(56) References Cited

U.S. PATENT DOCUMENTS

| | | | |
|---|---|---|---|
| 3,586,791 A | * | 6/1971 | Puharich |
| 4,352,960 A | | 10/1982 | Dormer et al. ........ 179/107 BC |
| 4,419,995 A | | 12/1983 | Hochmair et al. ...... 128/419 R |
| 4,495,384 A | | 1/1985 | Scott et al. ........... 179/107 FD |
| 4,499,339 A | | 2/1985 | Richard ............... 179/107 FD |
| 4,617,536 A | | 10/1986 | Richard .................... 332/37 D |
| RE32,947 E | | 6/1989 | Dormer et al. .......... 128/420.6 |
| 5,047,994 A | * | 9/1991 | Lenhardt |
| 5,571,148 A | * | 11/1996 | Loeb |
| 5,741,314 A | | 4/1998 | Daly et al. ................ 607/60 |
| 5,800,475 A | | 9/1998 | Jules .......................... 607/57 |
| 5,879,283 A | | 3/1999 | Adams et al. ............... 600/25 |
| 5,899,847 A | | 5/1999 | Adams et al. ............... 600/25 |
| 6,217,508 B1 | * | 4/2001 | Ball |
| 6,377,693 B1 | * | 4/2002 | Lippa et al. ............... 381/71.6 |
| 6,394,969 B1 | * | 5/2002 | Lenhardt |
| 6,406,439 B1 | * | 6/2002 | Cohen |
| 6,540,662 B2 | * | 4/2003 | Kroll |

OTHER PUBLICATIONS

Robert J. Fretz and Ralph P. Fravel, "Design and Function: A Physical and Electrical Description of the 3M House Cochlear Implant System," Ear and Hearing, vol. 6, No. 3 Supplement, pp. 14S-19S, copyright 1985.
Michael J. Danley and Robert J. Fretz, "Design and Functioning of the Single Electrode Cochlear Implant," pp. 21-26.
"Cochlear Implant System, Manual for Audiologists: Device Fitting and Adjustment," issued Feb. 1985, 3M Cochlear Implant System/ House Design, pp. i-IV9.

* cited by examiner

*Primary Examiner*—Suhan Ni
(74) *Attorney, Agent, or Firm*—Marger Johnson & McCollum P.C.

(57) ABSTRACT

A cochlear implant system for a patient's cochlea includes an external processor and an implanted internal unit. The internal unit includes one electrode for inserting in the patient's cochlea, and an internal coil for driving the electrode. The external processor includes a microphone for outputting electrical sound signals in response to ambient or other sounds, an oscillator for generating an electrical analog carrier signal, and a modulator for modulating the carrier signal with the sound signals to generate a modulated signal. An external coil couples magnetically the modulated signal to the internal coil. The analog carrier signal has a frequency in the ultrasonic human range, i.e. greater than 20 kHz, such as 32 kHz or 80 kHz. This sampling at higher frequency results in clearer rendering of sounds, and a higher frequency range of rendered sounds.

9 Claims, 5 Drawing Sheets

COCHLEAR IMPLANTS WITH A STIMULUS IN THE HUMAN ULTRASONIC RANGE AND METHOD FOR STIMULATING A COCHLEA

BACKGROUND OF THE INVENTION

1. Field of the Invention

The present invention is related to the field of hearing aids, and more specifically to the field of permanent cochlear implants for the hearing impaired.

2. Description of the Related Art

Hearing aids are often designed to amplify sound. These do not work, however, for patients with severe deafness because they cannot hear any sound, no matter how loud. For such patients, an implant technology is used, which stimulates directly the cochlea of the human ear.

The implant technology is now described in more detail with reference to FIG. 1. A human pinna (outer portion of the ear) 20 is supported on tissue 22 of the patient's head. When a sound 24 in the audible range of 20 Hz to 20,000 Hz reaches the pinna 20, the sound 24 reaches the eardrum 28 through an opening 26 in the tissue 22, known as the ear canal 26. In a healthy person, the eardrum 28 in turn excites the cochlea 30 mechanically, through additional structures (bones of hearing; not shown). The cochlea 30 accordingly stimulates the hearing nerve 31. In a severely deaf person, however, the cochlea 30 does not produce nerve stimulations, and thus the hearing nerve 31 transmits nothing to the brain.

A cochlear implant has two main parts, an internal unit 32 and an external unit 50. The internal unit 32 is surgically implanted near the pinna 20 of the patient. The internal unit 32 has at least one electrode 34 that is coupled with the cochlea 30. The internal unit 32 includes an internal coil assembly 40 for electrically driving the electrode 34. The internal unit 32 also includes a magnet 42.

The external unit 50 also includes a magnet 52, for suspending the external unit 50 from the field of the magnet 42. The external unit 50 also includes a microphone and signal processing component 54, and an external coil assembly 56. When the sound 24 reaches the microphone and signal processing component 54, the component 54 generates a signal which drives the external coil assembly 56. The signal is then inductively coupled ("injected") into the internal coil assembly 40.

Referring to FIG. 2, component 54 includes an oscillator 57, which generates a carrier analog signal. A volume control unit 58 is preferably implemented by an adjustable gain amplifier that amplifies the analog carrier signal. Adjusting the volume control unit 58 determines how much overall sound sensation, also known as percept, will reach the patient. In an older implementation of this cochlear implant, the amplified analog carrier signal is input into an amplitude modulator 60, to be amplitude modulated by the received sounds.

Component 54 also includes a microphone 62 with its associated circuitry, a preamplifier 64, and a band pass filter 66. The band pass filter 66 allows to pass only those frequencies of the preamplified electrical signal that correspond to sound in the range of 200 Hz-4000 Hz. The band pass filter 66 discards the signal corresponding to sound 24 that corresponds to the rest of the frequencies, that is, anything outside the frequency range of the band pass filter 66.

The filtered signal from band pass filter (BPF) 66 is input in a modulation control unit 68. The modulation control unit 68 thus uses the filtered signal to modulate the pre-amplified analog carrier signal in modulator 60. The modulator 60 output the modulated signal to an output amplifier 70. Thus amplified, the modulated signal is input into external coil assembly 56 of FIG. 1.

As described immediately above, the prior art limits how much sound percept can be delivered to the patient. This is now explained in more detail.

Referring also to FIG. 3, the interrelationship of the chosen frequencies is placed in perspective. A healthy ear can hear sounds between 20 Hz and 20 kHz (thus these are called the sonic, or hearable frequencies), which is denoted as a sonic range 78. The frequencies important to the understanding of speech belong within a speech range 80, reaching up to a frequency of 8 kHz. The carrier analog signal is denoted in FIG. 3 as an arrow 76, and is at a frequency of 16 kHz, which is within the sonic range 78.

Experiments using the above system showed that sound frequencies higher than 4,000 Hz sounded unclear to the user. Accordingly, the prior art included the band pass filter 66 (seen in FIG. 2), which has a BPF range 86 (seen in FIG. 3).

The result is that the prior art system only works for sounds within the BPF range 86 of the band pass filter 66. The prior art has rationalized this by concluding that the important portion of the sensitivity range of the human ear 78 is the portion where the speech range 80 belongs, and that further, the most important portion of the speech range 80 is found at 4,000 Hz and below.

Patients desire to be able to hear speech at the frequency higher than 4,000 Hz, and other sounds at frequencies higher than 8,000 Hz, just like healthy people.

BRIEF SUMMARY OF THE INVENTION

The present invention improves on the limitations of the prior art.

Generally, the present invention provides a cochlear implant system. The system includes an internal unit and an external unit. The internal unit includes at least one electrode for coupling with the patient's cochlea, and an internal (implanted) coil to inductively drive the electrode. The external unit includes a microphone for producing electrical signals in response to external sounds. In one embodiment of the invention, the external unit also includes an oscillator for generating an electrical analog carrier signal, and a modulator for modulating the carrier signal with the sound signals to generate a modulated signal. An external coil magnetically couples the modulated signal to the internal coil.

The analog carrier signal has a frequency in the ultrasonic human range, i.e. greater than 20,000 Hz, such as 32,000 Hz or 80,000 Hz. This higher frequency results in clearer rendering of sounds, and a higher frequency range of rendered sounds.

The foregoing and other objects, features and advantages of the invention will become more readily apparent from the following detailed description of a preferred embodiment, which proceeds with reference to the drawings.

DETAILED DESCRIPTION OF THE PREFERRED EMBODIMENT(S)

As has been mentioned, the present invention provides a cochlear implant system, a driver for cochlear implant system, and a method for stimulating a cochlea. The invention is now described with reference to FIGS. 4-7.

Figure 4:
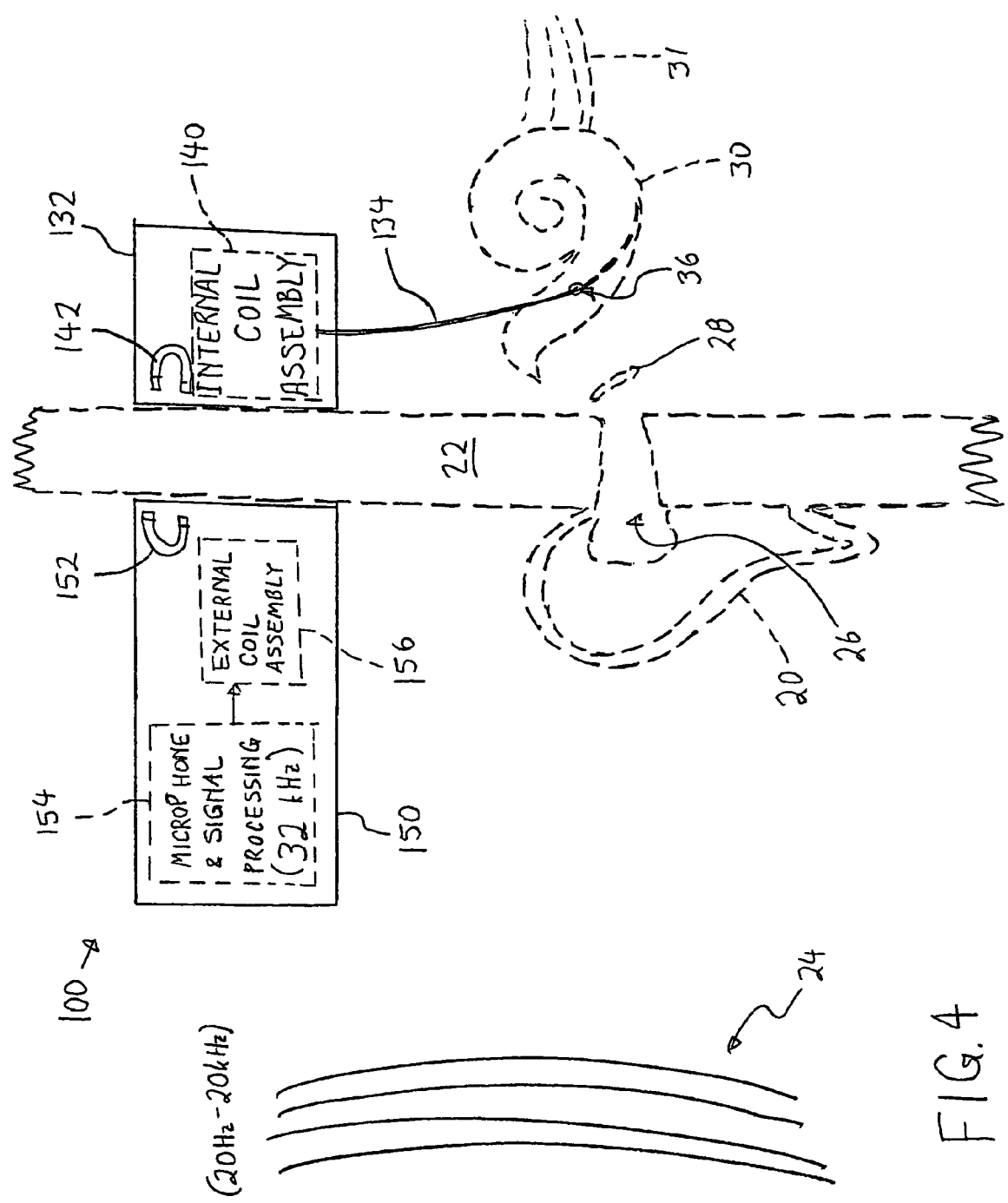
FIG. 4 is a partial section view of the patient using a cochlear implant system made according to an embodiment of the present invention.

Referring to FIG. 4, a cochlear implant system 100 of the invention is described in detail. The cochlear implant system 100 includes an internal unit 132 that is surgically implanted near the pinna 20 of the patient, and preferably close to the skin 22. The internal unit 132 has at least one active electrode 134 that is inserted into the cochlea 30 through hole 36. In addition, a second electrode (not shown) is optionally implanted in other nearby tissue, and used to provide a reference voltage to the active electrode 134.

The internal unit 132 includes an internal coil assembly 140 for electrically driving the electrode 134. In the preferred embodiment, the internal coil assembly 140 has two ends, one coupled to the active electrode 134, and the other coupled with the reference electrode (not shown). An advantage of the implant technology is that the internal coil assembly 140 can be driven externally. As such, there is no need for a battery, which would require changing after sometime. This permits implanting permanently the internal unit 132, with its sensitive contact of the cochlea 30.

The internal unit 132 also includes a magnet 142, which can be a simple magnet, or a more sophisticated magnet arrangement. The magnet 142 is so oriented that its strongest field is located outside the head, in a preferential direction (e.g., north vs. south vertically).

The cochlear implant system 100 of the invention further includes the driver 150, which is also known as an external unit 150. The driver 150 is for driving the implanted internal coil assembly 140, and therefore driving the electrode 134. The actual size of driver 150 can be as small in diameter as a U.S.A. penny, or even smaller. In FIG. 4, the external unit 150 is shown larger only for clarity.

In another embodiment, the invention provides only the driver 150, which would be used for patients who have already been implanted with cochlear implant systems using the prior art, which will thus perform better.

The external unit 150 is suspended in a spatial relation to the internal unit 132 by any means known in the art. Preferably, the external unit 150 includes a magnet 152 that interacts with the field of the magnet 142. The magnets 152 and 142 are thus used to suspend the external unit 150 on the tissue 22 of the patient, without any further support. Preferably, the magnets are arranged such that their polarities permit the driver 150 to be attached to a single, well-defined place on the tissue 22. If, however, the external unit 150 is suspended in a different way, then there is no need for either the internal unit 132 to have a magnet 142, or for the driver to have a magnet 152.

The external unit 150 includes a microphone and signal processing component 154, and an external coil assembly 156. The external unit 150 preferably includes a battery, which can be replaced as needed. When the sound 24 reaches the microphone and signal processing component 154, the component 154 generates a signal for driving the external coil assembly 156. The generated signal is an analog signal that is also known as electrical sound signal. The generated signal is thus coupled into the internal coil assembly 140. In other words, the external coil assembly 156 forms a transformer with the internal coil assembly 140, and inductively drives it.

Figure 5:
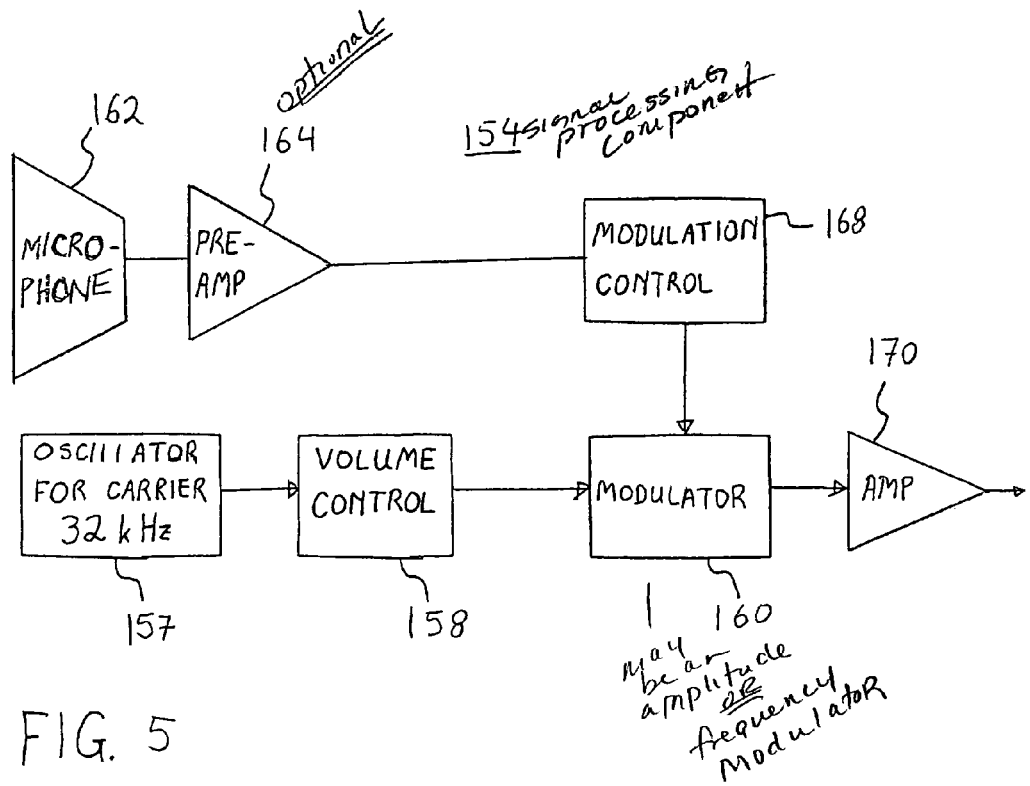
FIG. 5 is a block diagram for a circuit of a driver for a cochlear implant system made according to an embodiment of the present invention.

Referring to FIG. 5, the microphone and signal processing component 154 is described in detail. In one embodiment, component 154 includes an oscillator 157, which generates a carrier analog signal. The analog signal is continuous, and preferably sinusoidal. This is not limiting, however. The carrier analog signal of the invention can be triangular shaped, sawtooth shaped, etc. Such other shapes introduce additional, secondary carrier frequencies.

Importantly for the present invention, the carrier analog signal from oscillator 157 has a frequency greater than 20 kHz, i.e. it is outside the range of normal human hearing. One good operating value is 32 kHz. Higher values, such as 80 kHz, also work very well. The significance of this choice will be appreciated in view of the description pertaining to FIG. 6, later in this document.

Continuing to refer to FIG. 5, a volume control unit 158 is preferably implemented by an adjustable gain amplifier that amplifies the analog carrier signal. Adjusting the volume control unit 158 determines how much total sound percept will reach the patient. The amplified analog carrier signal is input into a modulator 160, to be amplitude modulated by the received sounds.

In one embodiment of the invention, modulator 160 is an amplitude modulator. In another embodiment of invention, modulator 160 is a frequency modulator. Stimulation by means of analog signals in the ultrasonic range can also be done directly, or in other ways, to provide the patient with a percept of sound.

Component 154 also includes a microphone 162 with its associated circuitry, and an optional preamplifier 164. The microphone 162 outputs an electrical signal responsive to the sounds 24 it receives. The preamplifier 164 amplifies the electrical signal of the microphone 162.

Figure 2:
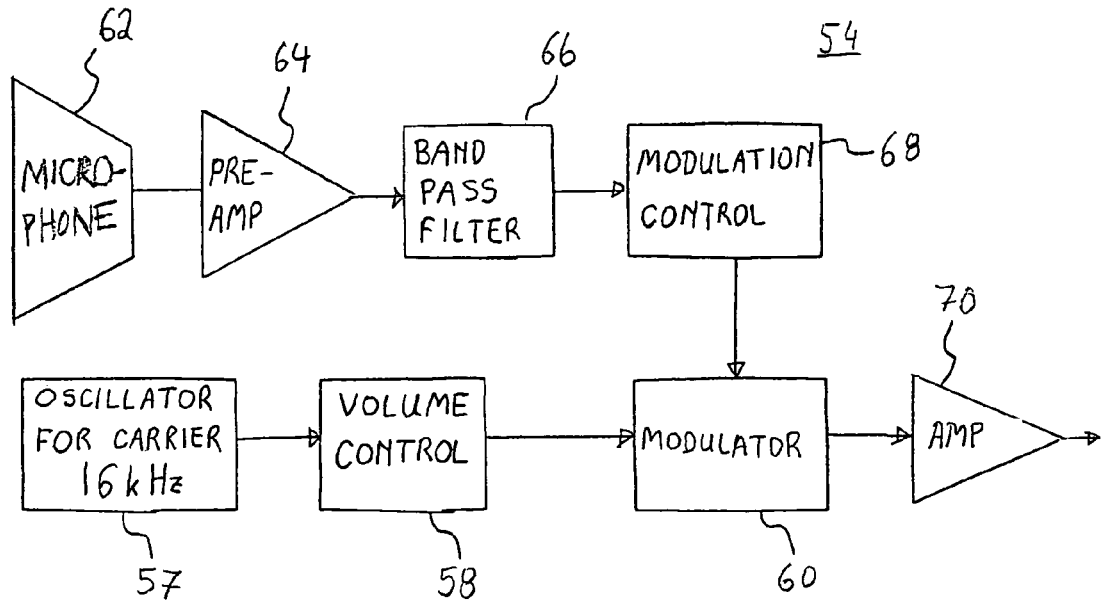
FIG. 2 is a block diagram of a microphone and signal processing component 54 of an external unit 50 of the prior implant technology of FIG. 1.

It should be noted that is no need for a band pass filter, such as band pass filter 66 of FIG. 2. Even if one is included, its upper limit can be much higher than that of the prior art, thus permitting a wider range of frequencies to be presented or perceived.

The signal from the preamplifier 164 is input in a modulation control unit 168. The modulation control unit 168 thus uses the signal to modulate the preamplified analog carrier signal in modulator 160. The modulator 160 outputs the modulated signal to an output amplifier 170. Thus amplified, the modulated signal is input into the external coil assembly 156 of FIG. 4.

Figure 3:
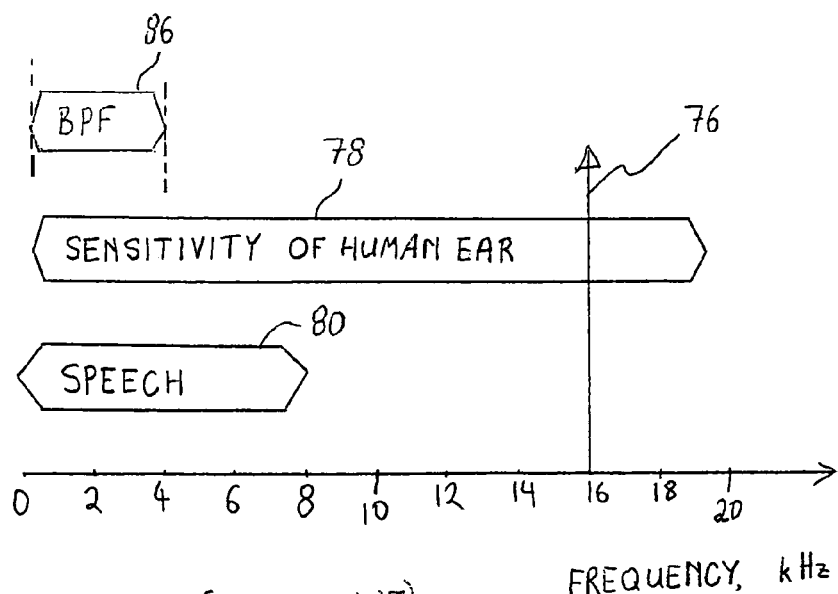
FIG. 3 is a graph showing the relative frequency ranges of the sensitivity of the human ear, speech, and a carrier frequency of an oscillator and a band pass filter in FIG. 2.

The superiority of the present invention is now explained by first analyzing further the weakness of the prior art system, as explained in FIG. 3. All the prior art globally adopted the carrier 76 to be at 16 kHz, within the sensitivity of human ear range 78. The prior art references universally treat the value of 16 kHz as an undisputed optimum.

Figure 1:
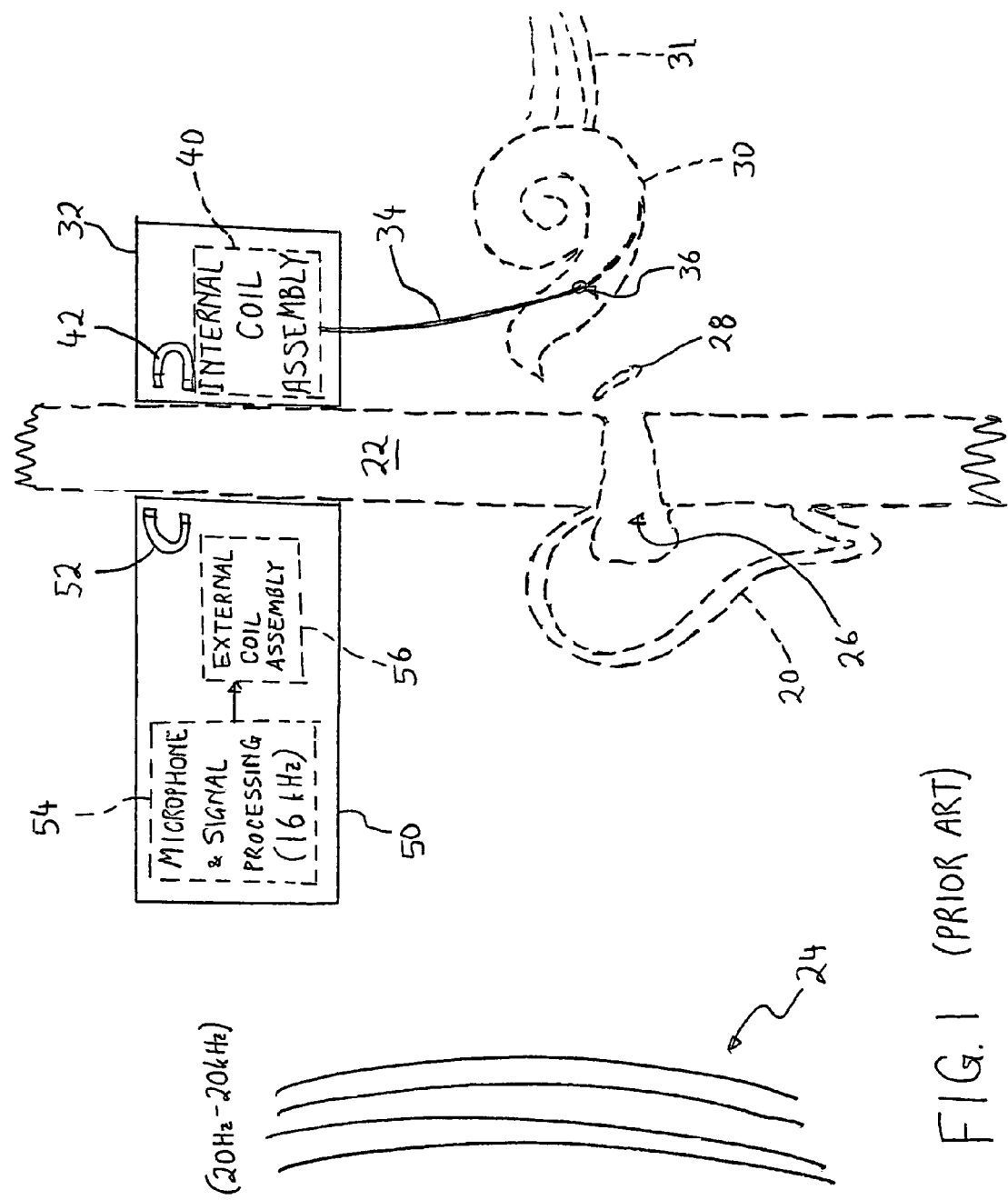
FIG. 1 is a partial section view of a patient using a prior implant technology.

The choice of the frequency of the carrier 76 imposes an upper limit as to the frequency that can be transmitted clearly. This results from the Nyquist limit. In other words, the carrier 76 samples the speech at its own frequency of 16 kHz. The higher the frequency of the sampled sound, the less clearly it will be rendered. For a frequency of 16 kHz, the Nyquist limit turns out to be ¼ of that, in other words 4 kHz. Indeed, the users of the prior art system of FIG. 1 found sounds having a frequency of higher than 4 kHz confusing.

Figure 6:
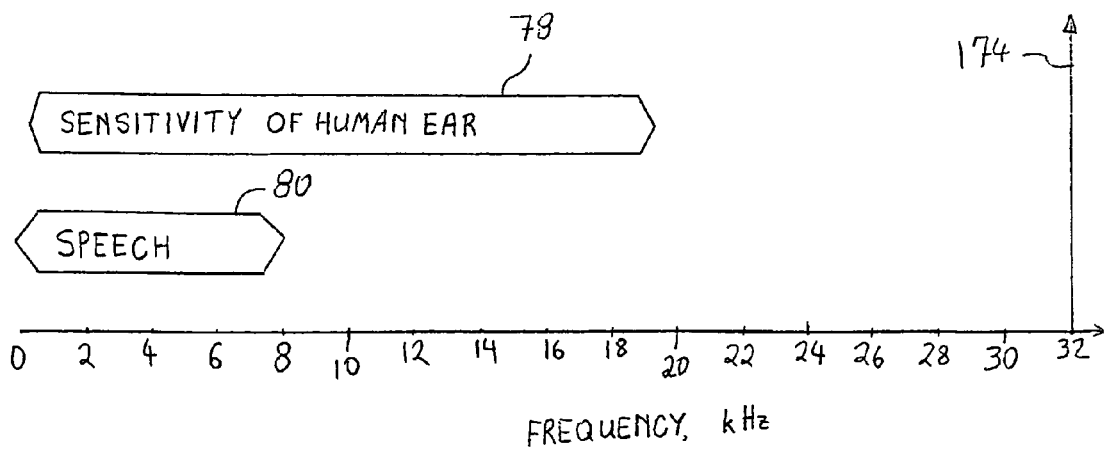
FIG. 6 is data showing the frequency of a carrier according to an embodiment of the present invention relative to the ranges of the sensitivity of the human ear and of speech.

Referring now to FIG. 6, the invention proposes that there is no reason for the carrier 174 produced by the oscillator 157 to be within the sound sensitivity frequency range of the human ear, or in the sonic range 78. As such, the carrier 174 is chosen to have a frequency of greater than 20 kHz. As can be seen from observing the ordinary human range 78, these frequencies for the carrier 174 belong in the human ultrasonic range.

It will be appreciated how the Nyquist limit permits a much higher range for the system of the present invention. In the embodiment of FIGS. 4, 5 and 6, the carrier frequency is 32 kHz, with a Nyquist limit of 8 kHz. This includes the entire range of speech 80, without limiting it, as the prior art did. It will now also be clear that, to match the sensitivity of the healthy human ear, the system of the invention should have a carrier frequency of (4×20 kHz) 80 kHz.

There is no need to stop there, either. A higher carrier frequency will permit the user to hear frequencies higher than any human has ever heard before. This can be extended to people who have no hearing deficit in the first place.

Other technical details for implementing the invention can be gleaned from the following publications, the disclosure of which is hereby incorporated herein by reference. These are:
U.S. Pat. Re. 32,947;
Design and Function: A Physical and Electrical Description of the 3M House Cochlear Implant System, Fretz & Fravel, Ear and Hearing, Vol. 6, No. 3 Supplement, pp. 14S-19S, 1985;
DESIGN AND FUNCTIONING OF THE SINGLE—ELECTRODE COCHLEAR IMPLANT, Danley & Fretz, pp. 21-26;
COCHLEAR IMPLANT SYSTEM, Series 7700 House Design, Manual for Audiologists: Device Fitting and Adjustment, 3M, 1985.

Figure 7:
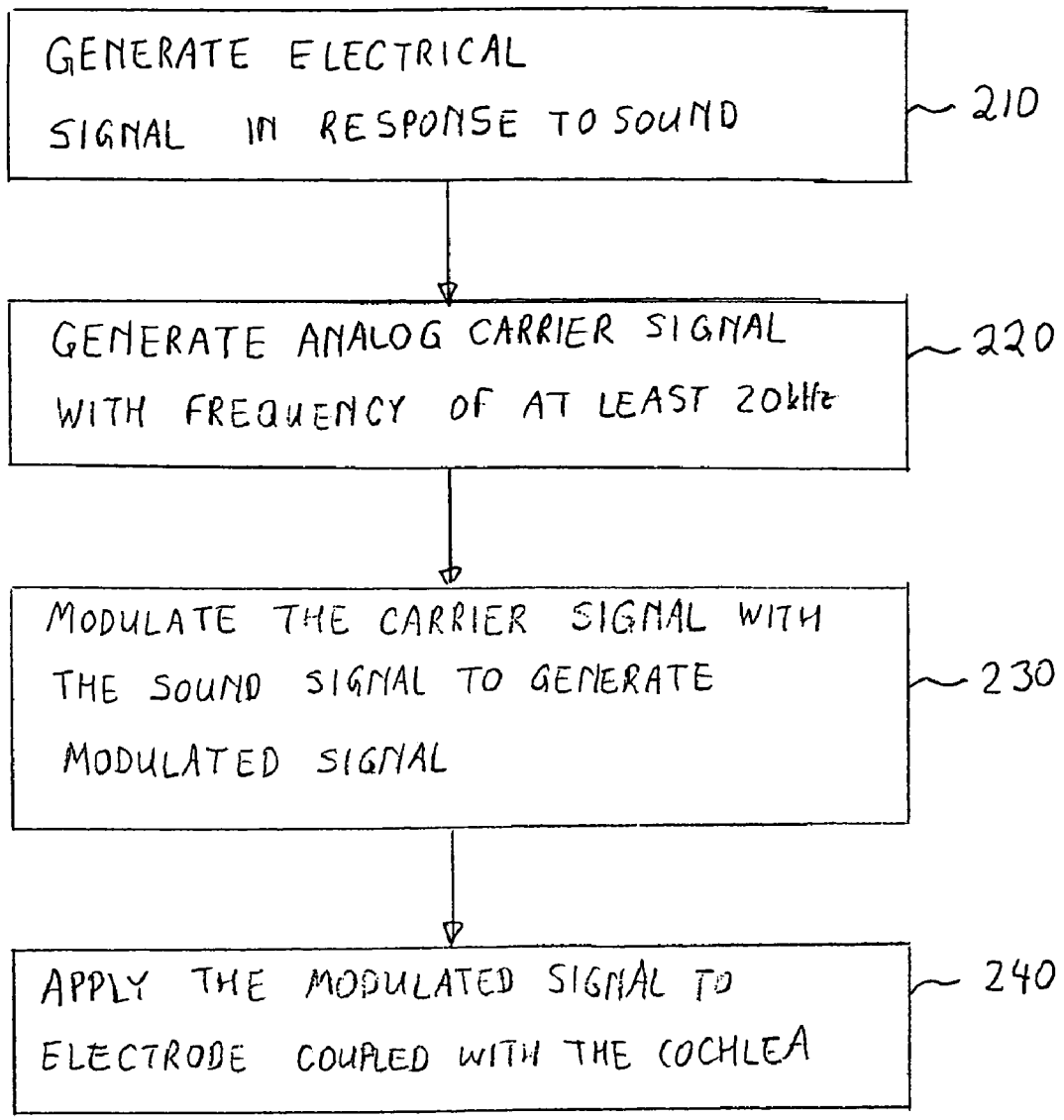
FIG. 7 is the flowchart for illustrating a method according to an embodiment of the present invention.

Referring to FIG. 7, a method according to the invention is now described for stimulating the cochlea in response to sound.

According to box 210, an electrical signal, also known as an electrical sound signal, is generated in response to the sound. This can be accomplished with a microphone, and associated circuitry.

According to box 220, an electrical analog carrier signal is generated having a frequency of greater than 20 kHz. This can be accomplished with an oscillator. The frequency can be 21 kHz, 32 kHz, 80 kHz, or whatever frequency is deemed suitable for the desired application.

According to box 230, the carrier signal is modulated with the sound signal to generate a modulated signal. Modulating can be by amplitude modulation or frequency modulation.

According to box 240, the modulated signal is applied to an electrode that is coupled with the cochlea.

In this description numerous details have been set forth in order to provide a more thorough understanding of the invention. A person skilled in the art will be able to practice the present invention in view of the present description and the incorporated references. In other instances, well-known features have not been described in detail in order not to obscure unnecessarily the invention.

The inventor regards the subject matter of the invention to include all combinations and sub-combinations of the various elements, features, functions and/or properties disclosed herein. While the invention has been disclosed in its preferred form, the specific embodiments thereof as disclosed and illustrated herein are not to be considered in a limiting sense. Indeed, it should be readily apparent to those skilled in the art in view of the present description that the invention can be modified in numerous ways.

The following claims define certain combinations and sub-combinations of these elements, which are regarded as novel and non-obvious. Additional claims for other combinations and sub-combinations of features, functions, elements and/or properties may be presented in this or in a related document.

The invention claimed is:

1. A cochlear implant system for a patient's cochlea comprising:
at least one electrode for electrical coupling with the patient's cochlea;
an internal coil for implanting in the patient to drive the at least one electrode;
a microphone for outputting electrical sound signals in response to external sounds;
an oscillator for generating an electrical analog carrier signal having a frequency greater than 20 kHz;
a modulator for modulating the carrier signal with the sound signals to generate a modulated signal; and
an external coil for magnetically coupling the modulated signal to the internal coil such that the modulated signal is electrically directly applied to the cochlea to cause a percept.

2. The system of claim 1, wherein the modulator is an amplitude modulator.

3. The system of claim 1, wherein the modulator is a frequency modulator.

4. The system of claim 1, wherein the electrical analog carrier signal has a frequency of at least 32 kHz.

5. The system of claim 4, wherein the modulator is an amplitude modulator.

6. The system of claim 4, wherein the modulator is a frequency modulator.

7. The system of claim 1 comprising at least one reference electrode for providing a reference voltage to the at least one electrode.

8. The system of claim 7 where the internal coil includes a first terminal for connecting to the at least one electrode and a second terminal for connecting to the at least one reference electrode.

9. The system of claim 1 wherein the modulated signal allows a wearer of the implant system to hear frequencies higher than air-conducted sonic human hearing sensitivity.

* * * * *